United States Patent [19]

Misaki et al.

[11] Patent Number: 4,978,609
[45] Date of Patent: Dec. 18, 1990

[54] MONOCLONAL ANTIBODY SPECIFIC TO HUMAN PANCREATIC PHOSPHOLIPASE $A_2$

[75] Inventors: Atsushi Misaki; Masao Kono; Michio Ogawa, all of Osaka; Mitsuhiro Okamoto, Nara, all of Japan

[73] Assignee: Shionogi & Co., Ltd., Osaka, Japan

[21] Appl. No.: 173,536

[22] Filed: Mar. 25, 1988

[30] Foreign Application Priority Data

Apr. 15, 1987 [JP] Japan .................................. 62-93586

[51] Int. Cl.$^5$ ........................ C01N 33/053; C12N 5/00
[52] U.S. Cl. ....................................... 435/7; 436/548; 435/387; 435/240.27; 435/68
[58] Field of Search .................. 435/68, 170.2, 240.27, 435/7; 530/387; 436/548

[56] References Cited

PUBLICATIONS

Sevier, et al., Clin. Chem. 27 (11), 1981, pp. 1797–1806.
Nishiyima, et al., J. Biochem 94, 1983, pp. 137–147.
Eskola, et al., Clin. Chem. 29 (10), 1983, pp. 1777–1780.
Trends in Biochemical Sciences, vol. 7, No. 12, pp. 419–420 (1982).
Trends in Biotechnology, vol. 3, No. 7, pp. 170–175 (1985).

*Primary Examiner*—Christine Nucker
*Assistant Examiner*—Karen I. Krupen
*Attorney, Agent, or Firm*—Birch, Stewart, Kolasch & Birch

[57] ABSTRACT

The present invention relates to monoclonal antibodies having high affinity to human pancreatic $PLA_2$, the production thereof, hybridomas producing them and an immunoassay for human pancreatic $PLA_2$ using them.

10 Claims, 1 Drawing Sheet

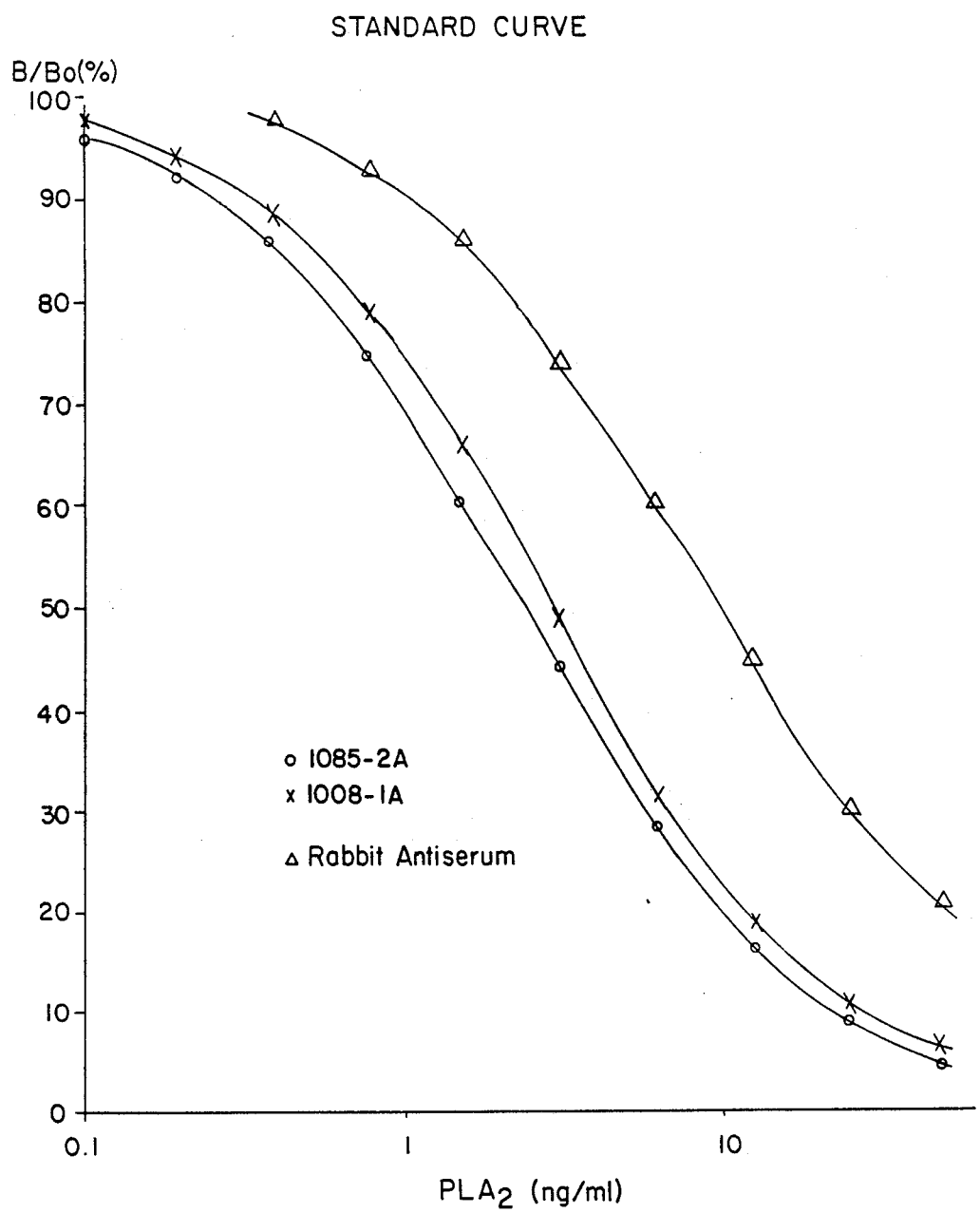

MONOCLONAL ANTIBODY SPECIFIC TO HUMAN PANCREATIC PHOSPHOLIPASE $A_2$

BACKGROUND OF THE INVENTION

1. Field of the Invention

The present invention relates to a monoclonal antibody specific to human pancreatic phospholipase $A_2$, its production, a hybridoma for producing it and an assay of human pancreatic phospholipase $A_2$ using it.

2. Discussion of Prior Art

Phospholipase $A_2$ (hereinafter referred to as $PLA_2$) is an enzyme hydrolyzing diacylglycerophospholipid in an ester linkage at the second position. $PLA_2$ is roughly classified into intracellular or membraneous $PLA_2$ and $PLA_2$ secreted from the pancreas as a digestive enzyme. The latter is produced as prophospholipase $A_2$ in the pancreatic acinar cell and secreted into pancreatic duct. Then it is hydrolyzed mainly by trypsin in the duodenum to cleave the amino terminal peptide chain comprising 7 amino acid residues to give active $PLA_2$. Isolation of human pancreatic $PLA_2$ from the pancreas and pancreatic juice has previously been reported (Magee, W. L. et al, Biochem. J. 83, 17–25, 1962; Grataroli, R. et al, Biochimie 63, 677–684, 1981; Nishijima, J. et al, J. Biochem., 94, 137–147, 1983 and so on).

It has been reported that in pancreatitis the blood level of pancreatic $PLA_2$ is elevated. Accordingly, the assay of pancreatic $PLA_2$ can be utilized in diagnosing acute abdominal diseases including acute pancreatitis.

Hitherto, pancreatic $PLA_2$ in serum has been assayed the enzymatically. However, enzymatic activity of pancreatic $PLA_2$ in the serum is low and, therefore, the assay requires a long and complicated procedure, which makes it practically impossible to clinically apply the assay for the diagnosis of an acute abdomen.

As an immunoassay of pancreatic $PLA_2$, the radioimmunoassay by Nishijima et al (J. Biochem. 94, 137–147, 1983) and the fluoroimmunoassay by Eskola et al (Clin. Chem. 29, 1777, 1983) have already been reported. According to both methods, the blood level of $PLA_2$ in acute pancreatitis is higher than the normal level. This fact suggests that the immunoassay can be applied for diagnosing acute abdomen including acute pancreatitis.

As described above, human pancreatic $PLA_2$ has been able to be assayed immunologically in some instances. However, the antibodies used in the above reports are polyclonal antibodies (rabbit antiserum). A polyclonal antibody is inferior to a monoclonal antibody in terms of specificity, equality and stable supply. Moreover, if a monoclonal antibody having a high affinity is obtained, it becomes possible to develop a more simple and quick assay method for human pancreatic $PLA_2$.

SUMMARY

The present invention provides monoclonal antibodies having high affinity to human pancreatic $PLA_2$, the production thereof, hybridomas producing them and an immunoassay for human pancreatic $PLA_2$ using them. The hybridomas of the present invention which produce anti-human pancreatic $PLA_2$ monoclonal antibody are thoroughly cloned cell lines. By culturing them the monoclonal antibodies described above are effectively manufactured. By using the monoclonal antibodies in an immunoassay such as a radioimmunoassay and the like, the quick diagnosis of acute abdomen including acute pancreatitis becomes possible.

BRIEF DESCRIPTION OF THE DRAWING

FIG. 1 shows the standard curve of pancreatic $PLA_2$ in a radioimmunoassay using a monoclonal or a polyclonal antibody.

DETAIL DESCRIPTION OF THE INVENTION

The present invention provides a monoclonal antibody having a high affinity and specificity for human pancreatic $PLA_2$ and an assay method which is effective for the diagnosis of acute pancreatitis and so on.

Taking the above situation into consideration, the present inventors have obtained a monoclonal antibody having high affinity and specificity.

The anti-human pancreatic $PLA_2$ monoclonal antibody of the present invention is produced by a hybridoma which is prepared by fusing a myeloma cell with a lymphocyte obtained from human pancreatic $PLA_2$-immunized mice.

In order to obtain the monoclonal antibody of the present invention, it is necessary to purify human pancreatic $PLA_2$ as an immunogen. The purification can be achieved according to the methods described in the above mentioned reports.

A laboratory animal such as a mouse is immunized with the refined human pancreatic $PLA_2$ as an immunogen. The immunization may be effected in a usual manner, for example, an emulsion prepared by mixing the antigen in physiological saline with Freund's complete adjuvant is injected.

B lymphocyte is prepared from the animal immunized according to the above manner and fused with a permanent myeloma cell line. This fusion may be performed according to the usual method (Köhler and Milstein, Nature 256, 495–497, 1975). From the obtained hybridomas, a hybridoma producing anti-human pancreatic $PLA_2$ antibody is selected.

This selection is achieved by assaying anti-human pancreatic $PLA_2$ antibodies in culture supernatant by suitable methods such as an enzyme linked immunosorbent assay (ELISA) and radioimmunoassay. Hybridomas in the supernatant of which anti-human pancreatic $PLA_2$ antibody is detected are multiplied to about 10 ml of medium and frozen for preservation. At the same time the supernatant is recovered and the properties of the antibody in the supernatant is examined to select a hybridoma producing the monoclonal antibody having the desired properties. The selected hybridoma is cloned by the usual methods such as the limiting dilution to establish the cell line. The established cell line is transplanted into the abdominal cavity of the same species of animal as used in the immunization to obtain the ascites containing a high concentration of the antibody or cultured in a medium to obtain the antibody from the cultured medium.

The thus prepared antibody may be refined as the occasion demands, for example, by the usual method such as ammonium sulfate-fractionation, ion-exchange chromatography, protein A column chromatography and the like.

In the present invention, anti-human pancreatic $PLA_2$ antibody-producing mouse hybridoma cell lines 1008-1 and 1085-2 and monoclonal antibodies 1008-1 and 1085-2 produced thereby were obtained according to the above method.

The thus obtained hybridoma cell lines have been deposited having the following accession numbers with the European Collection of Animal Cell Cultures (ECACC) at PHLS CAMR, Porton Down, Salisbury, SP4 OJG., Great Britain under the Budapest Treaty since Apr. 8, 1987.

Hybridoma 1008-1:87040803
Hybridoma 1085-2:87040802

Monoclonal antibodies 1008-1 and 1085-2 have the following properties:

(1) Immunoglobulin class and subclass is $IgG_1$ and L chain is of $\kappa$ type.

(2) The binding constants of 1008-1 and 1085-2 are $4 \times 10^{11} M^{-1}$ and $1 \times 10^{12} M^{-1}$, respectively. Both have high affinity.

(3) Both monoclonal antibodies have no cross reactivity with porcine pancreatic $PLA_2$ and Naja naja venom (Indian cobra venom) $PLA_2$ and specific to human pancreatic $PLA_2$.

Thus, the monoclonal antibodies of the present invention are specific to human pancreatic $PLA_2$ and show very high affinity thereto. Therefore, they are very useful in the immunoassay of human pancreatic $PLA_2$.

When $PLA_2$ in human serum is measured by the radioimmunoassay utilizing ascites 1008-1A or 1085-2A, in the case using 1008-1A the $PLA_2$ the concentration is $2.6 \pm 0.7$ ng/ml in normal adults and $44.1 \pm 34.0$ ng/ml in acute pancreatitis patients and in the case using 1085-2A, $0.8 \pm 0.2$ ng/ml and $23.8 \pm 14.7$ ng/ml, respectively. In both cases the latter is clearly higher than the former.

The result shows that the immunoassay such as radioimmunoassay and enzyme immunoassay using the monoclonal antibody of the present invention can be applied to the diagnosis of acute pancreatitis. Moreover, by utilizing high affinity of the monoclonal antibodies of the present invention a quick and simple immunoassay for human pancreatic $PLA_2$ can be developed and utilized in the diagnosis of acute pancreatitis.

Since it is not difficult for one of ordinary skill in the art to prepare hybridomas and monoclonal antibodies having the properties similar to those of the present invention, such hybridomas and monoclonal antibodies as having the similar properties are included in the scope of this invention.

EXAMPLE

Example 1: Preparation of Hybridoma Producing Anti-Human Pancreatic $PLA_2$ Monoclonal Antibody and Production of the Antibody (1) Preparation of Antigen Human pancreatic $PLA_2$ useful as an antigen was purified from human pancreatic juice according to the method of Nishijima et al (J. Biochemistry 94, 137–147, 1983).

(2) Immunization

Human pancreatic $PLA_2$ in physiological saline ($PLA_2$ concentration 0.5 mg/ml) was emulsified with the same volume of Freund's complete adjuvant, 0.1 ml of which was subcutaneously injected to the back of BALB/c mouse (female, 5 weeks old) 3 times at intervals of 3 weeks. The dose of $PLA_2$ was 25 $\mu$g per mouse. Further, 5 weeks after the third immunization 50 $\mu$g of human pancreatic $PLA_2$ dissolved in 200 $\mu$l of physiological saline was injected into the abdominal cavity as a booster.

(3) Fusion

Four days after the booster, the spleen of the mouse was enucleated and the cells were kept in 0.17M ammonium chloride with ice-cooling for 5 min to destroy the erythrocytes. The remaining cells were suspended in RPMI 1640 medium to prepare spleen lymphocytes to be used in cell-fusion. Next, 8-azaguanine-resistant myeloma cells (NS-1, $7 \times 10^7$ cells) suspended in RPMI 1640 were mixed with the spleen cells ($1.4 \times 10^8$ cells), which was centrifuged at 1000 rpm for 10 min. After the supernatant was removed, 0.8 ml of 50% polyethyleneglycol (molecular weight 4000, Merck) dissolved in RPMI 1640 was added to the cell pellet in 1 min while stirring with a pipet and further stirred for 1.5 min. Then, 2 ml of RPMI 1640 was added thereto in 2 min while stirring and an additional 2 ml in 1 min. Further, 18 ml of RPMI 1640 was added dropwise thereto while gently stirring. After the centrifugation (1000 rpm, 10 min), the supernatant was removed and the cells sedimented were suspended in 70 ml of HAT medium (RPMI 1640 containing 20% FCS, $1 \times 10^{-4}$M hypoxanthine, $4 \times 10^{-7}$M aminopterin, $1.6 \times 10^{-5}$M thymidine), 0.1 ml of which was distributed to each well of 7 96-well cell culture plates (Coaster). In the cell culture plates mouse spleen cells suspended in HAT medium ($1 \times 10^5$ cells/0.1 ml/well) were previously placed as feeder cells. After that, a half amount of the HAT medium was replaced by a fresh one at intervals of a few days. About 10 days later, the growth of hybridomas was observed. The number of wells in which hybridomas grew was 508 (75%).

(4) Selection of hybridoma

It was determined by ELISA if anti-human pancreatic $PLA_2$ antibody was produced in the well in which hybridomas grew, using the supernatant. To each well of 96-well flat-bottom ELISA plate (Nunc) was added 50 $\mu$l of human pancreatic $PLA_2$ solution (10 ng/50 $\mu$l of 0.05M sodium carbonate buffer, pH 8.5) and allowed to stand overnight at 4° C. to immobilize the human pancreatic $PLA_2$ to the plate. After removing the supernatant, 100 $\mu$l of PBS containing 0.2% bovine serum albumin was added thereto and allowed to stand at room temperature for 1 hr. Each well was washed twice with PBS containing 0.1% Tween 80, to which was added about 50 $\mu$l of the supernatant of the well in which hybridoma grew and allowed to stand at 37° C. for 30 min. After washing these wells twice, 50 $\mu$l of biotinylated anti-mouse immunoglobulin antibody (Vectastain ABC kit, Funakoshi Yakuhin Kabusikigaisha) was added to each well and allowed to stand at room temperature for 15 min. After washing twice, 50 $\mu$l of a solution of complex of avidin with biotinylated horseradish peroxidase was added thereto and allowed to stand at room temperature for 15 min. These wells were washed 5 times, to which was added 100 $\mu$l of a substrate solution (0.05M citrate-phosphate buffer (pH 5.3) containing 0.02% ABTS and 0.03% hydrogen peroxide) and allowed to stand at room temperature for 20 min. Finally, 100 $\mu$l of 2 mM sodium azide was added to each well and stirred and the absorbance at 415 nm was measured by a plate reader (MTP-22, Corona Electric Co. Ltd.).

(5) Freezing of hybridoma for preservation

The hybridomas that the activity of anti-human pancreatic $PLA_2$ antibody was observed in their well by the above ELISA were expanded the HT medium (aminopterin was removed from the HAT medium described above,) to about 10 ml of the medium, which were suspended in 1 ml of the medium for freezing (bovine serum albumin containing 10% DMSO) and frozen at −80° C. for preservation. Each supernatant was recovered and preserved in order to examine the property of the produced antibody. Eighty five kinds of hybridomas in all were preserved.

(6) Displacement test of supernatant

Serial dilution (100 μl) of the supernatants which were recovered in preserving hybridomas as mentioned above were mixed with 100 μl of $^{125}$I-labelled human pancreatic $PLA_2$ (described in the example 5 (1)) and the assay buffer (described in the example 5 (1)) containing 2% bovine gamma globulin and incubated at room temperature overnight. Then, 250 μl of an aqueous solution of 27% polyethyleneglycol 6000 was added thereto and immediately stirred. After centrifugation at 3000 rpm for 20 min, the supernatant was removed by suction. The radioactivity of the precipitate was measured to calculate the ratio of $^{125}$I-labelled human pancreatic $PLA_2$ bound to the antibody. At the same time, the same test was performed using 100 μl of the assay buffer containing 5 ng/100 μl of human pancreatic $PLA_2$ and 2% bovine gamma globulin instead of the assay buffer containing 2% bovine gamma globulin and the decrease of the radioactivity of $^{125}$I-labelled human pancreatic $PLA_2$ from the precipitate, that is, the extent of displacement of $^{125}$I-labelled human pancreatic $PLA_2$ by the supplemented human pancreatic $PLA_2$ was examined. The supernatant that the ratio of the displacement was high was regarded as containing high affinity antibody.

(7) Cloning

Hybridomas which were regarded as producing high affinity antibody by the result of the above displacement test were reconstituted from frozen samples and cloned by the limiting dilution. In the 96-well cell culture plate the hybridomas were cultured at a concentration of 1 cell/200 μl/well. The ELISA described above was performed on the supernatant of the well in which hybridomas grew as a sole colony. The hybridomas of the wells in which the activity of anti-human pancreatic $PLA_2$ antibody was observed were expanded by culture. Thus, the hybridoma cell lines 1008-1 and 1085-2 which produce anti-human pancreatic $PLA_2$ antibody were established.

(8) Preparation of ascites containing antibody

The established hybridomas were transplanted into the abdominal cavity of the mouse in order to prepare ascites containing antibodies in a high concentration. Into a mouse (BALB/c, female, into which 0.5 ml of pristane was intraperitoneally injected 10 days before) were intraperitoneally injected about $1 \times 10^7$ hybridomas suspended in RPMI 1640. The ascites were recovered 1–3 weeks later and the cells in the ascites were removed therefrom. To the supernatant was added sodium azide by 0.1% and the resultant material was frozen for preservation. Thus, the ascites 1008-1A and 1085-2A containing the monoclonal antibodies in a high concentration, which were produced by the hybridomas 1008-1 and 1085-2, respectively, were prepared.

(9) Purification of monoclonal antibody

Antibodies were purified from the ascites 1008-1A and 1085-2A by Affi-Gel Protein A MAPS-II kit (BIO-RAD). Using 2 ml of the gel, 1 ml of each of the ascites was purified according to the procedure of the kit and about 2 mg and about 5 mg of antibodies were obtained from 1008-1A and 1085-2A, respectively. The purity of the antibody was examined by SDS-polyacrylamide electrophoresis. The purified antibody fraction was reduced with 2-mercaptoethanol and applied to 12.5% SDS electrophoresis. As a result, 2 bands of H chain around a molecular weight of about 52000 and an L chain around a molecular weight of about 28000 were observed.

Example 2: Determination of Class and Subclass of Monoclonal Antibody

The determination of the class and the subclass of the immunoglobulin produced by the hybridoma was achieved by the ELISA described above, using rabbit antibody specific to the class and the subclass of mouse immunoglobulin and peroxidase-conjugated goat anti-rabbit antibody (MonoAb-ID EIA Kit, Zymed Laboratories). As a result, in both cases of the ascites 1008-1A and 1085-2A development for color was observed when anti-$\gamma_1$ antibody and anti-$\kappa$ antibody, were used.

Example 3: Affinity of Monoclonal Antibody

According to the procedure of the example 5 (2), a standard curve was prepared and the radioactivity of precipitate/radioactivity of supernatant and the concentration of the antigen bound to the antibody were plotted in the ordinate and the abscissa, respectively, for each concentration of human pancreatic $PLA_2$ according to the scatchard method. The affinity constant of the antibody was calculated from the slope of the resulting line.

Example 4: Specificity of Monoclonal Antibody

By using porcine pancreatic $PLA_2$ (Boehringer Mannheim GmbH) and Naja naja venom $PLA_2$ (Sigma) instead of a sample for the radioimmunoassay of human pancreatic $PLA_2$ in the example 5 (2), the displacement of $^{125}$I-labelled human pancreatic $PLA_2$ was examined. As a result, in both cases of 1008-1A and 1085-2A, the displacement of $^{125}$I-labelled human pancreatic $PLA_2$ was not observed at all where 2 kinds of $PLA_2$ described above were added at a thousand times as much as 50% inhibitory concentration in the case of human pancreatic $PLA_2$.

Example 5: Radioimmunoassay Using Monoclonal Antibody (1) Preparation of $^{125}$I-labelled human pancreatic $PLA_2$ $^{125}$I-labelled human pancreatic $PLA_2$ was prepared by the chloramine-T method according to the usual method of Hunter and Greenwood (Nature 194, 495–496, 1962).

Reagent:
Human pancreatic $PLA_2$: 0.5 mg/ml 0.5M phosphate buffer, pH 7.5
Na$^{125}$I: 1 mCi/10 μl (Amersham)
Chloramine-T: 2 mg/ml 0.5M phosphate buffer, pH 7.5
Sodium pyrosulfite: 2.5 mg/ml 0.5M phosphate buffer, pH 7.4
Bovine serum albumin: 10 mg/ml 0.1M phosphate buffer, pH 7.4
KI: 100 mg/ml distilled water
Assay buffer:
0.01M phosphate buffer (pH 7.4) containing 0.2% bovine serum albumin, 5 mM ethylenediamine tetraacetate, 0.01% sodium azide and 0.9% NaCl
Freeze-drying buffer:
5 times as dense as the assay buffer
Method:

To a tube 25 μl of 0.5M phosphate buffer (pH 7.5), 10 μl of human pancreatic PLA$_2$ (5 μg) and 5 μl of Na$^{125}$I (500 μCi) were added and stirred. To the resultant was added 5 μl of chloramine-T (10 μg) and stirred for 45 sec, to which was added 25 μl (62.5 μg) of sodium pyrosulfite and stirred. Then, 5 μl (50 μg) of bovine serum albumin and 5 μl (500 μg) of KI were added thereto and stirred. The reaction mixture was applied to Sephadex G-25 column (1 cm diameter×25 cm length) to separate $^{125}$I-labelled human pancreatic PLA$_2$ and $^{125}$I− ion. The fraction of $^{125}$I-labelled human pancreatic PLA$_2$ was diluted to 2.5 μCi/2 ml with freeze-drying buffer, 2 ml of which was distributed to a vial, freeze-dried and preserved at 4° C. Before use, it was dissolved in 10 ml of distilled water for dissolving.

(2) Radioimmunoasay of human pancreatic PLA$_2$
Reagent:
Dilution of ascites: 1008-1A (diluted 360000 times with assay buffer) and 1085-2A (diluted 800000 times with assay buffer)
Human pancreatic PLA$_2$ standard: Assay buffer containing human pancreatic PLA$_2$ at a concentration of twofold dilution in a range of 0.1–25 ng/ml
$^{125}$I-labelled human pancreatic PLA$_2$: described in (1)
Assay buffer: described in (1)
Immunobeads: Rabbit anti-mouse immunoglobulin (BIO-RAD), used as a 1 mg/ml slution diluted with assay buffer Method:
In a tube was placed 100 μl of human pancreatic PLA$_2$ standard or sample to which 200 μl of assay buffer, 100 μl of $^{125}$I-labelled human pancreatic PLA$_2$ and 100 μl of diluted ascites (1008-1A or 1085-2A) were added. After mixing, it was incubated overnight at room temperature. Then, 100 μl of immunobeads was added thereto and allowed to stand at room temperature for 2 hr. After centrifuging at 3000 rpm for 10 min and removing the supernatant, the radioactivity of the precipitate was measured by a gamma counter (Aloka, ARC-600). From the standard curve made by using human pancreatic PLA$_2$ standard the concentration of human pancreatic PLA$_2$ in the sample was calculated.

Standard Curve
The standard curve of radioimmunoassay is shown in FIG. 1. The sensitivity (90% inhibitory concentration) in cases of using 1008-1A and 1085-2A was 0.4 ng/ml and 0.3 ng/ml, respectively, which indicates the curve is highly sensitive.

Assay of human serum
Sera of normal adults, patients with acute pancreatitis and patients from whom the whole pancreas is enucleated, which were used undiluted or diluted with the assay buffer to be used, were assayed by the radioimmunoassay. The results are shown in Table 1.

TABLE 1

Concentrations of human pancreatic PLA$_2$ in several kinds of human sera measured by the radioimmunoassay using the monoclonal antibodies

| Monoclonal antibody (ascites) | Normal Adults (N = 5) | Patients with Acute Pancreatitis (N = 8) | Patients from whom the pancreas is enucleated (N = 3) |
| --- | --- | --- | --- |
| 1008-1A | 2.6 ± 0.7 | 44.1 ± 34.0 | 0.2 ± 0.05 |
| 1085-2A | 0.8 ± 0.2 | 23.8 ± 14.7 | 0.1 ± 0.1 |

Mean ± S.D. (ng/ml)

The concentration in serum of patients with acute pancreatitis was higher than that of normal adults in both radioimmunoassays using 1008-1A and 1085-2A. Thus, these 2 monoclonal antibodies proved to be useful in the diagnosis of acute pancreatitis.

Since the concentrations of the patients from whom the whole pancreas was enucleated were under the detection limit, these monoclonal antibodies proved to be highly specific to human pancreatic PLA$_2$.

Referential Examination: Radioimmunoassay Using Rabbit Antiserum

A standard curve was made using rabbit antiserum in a similar manner to example 5 except for the following:
Diluted ascites→Diluted antiserum: diluted 40000 times with the assay buffer
Human pancreatic PLA$_2$ standard: Assay buffer containing human pancreatic PLA$_2$ at a concentration of twofold dilution in a range of 0.39–100 ng/ml
Immunobeads: Goat anti-rabbit immunoglobulin (BIO-RAD), diluted with the assay buffer to 1 mg/ml The results are shown in FIG. 1. The 90% inhibitory concentration of the standard curve by rabbit antiserum was 1.0 ng/ml. Those of 1008-1A and 1085-2A are 0.3 ng/ml, respectively, and, therefore, the monoclonal aitibodies 1008-1A and 1085-2A, they are more sensitive than the rabbit antiserum.

What we claim is:
1. A monoclonal antibody specific to human pancreatic phospholipase A$_2$ having an affinity constant greater than $10^{11}$ M$^{-1}$.
2. The monoclonal antibody of claim 1, of which subclass is IgG$_1$.
3. The monoclonal antibody of claim 1, of which L chain is of K type.
4. The monoclonal antibody of claim 1, which does not react with either porcine pancreatic phospholipase A$_2$ or Naja naja venom phospholipase A$_2$.
5. The monoclonal antibody of claim 1, which is monoclonal antibody 1008-1 produced by hybridoma 1008-1 or monoclonal antibody 1085-2 produced by hybridoma 1085-2.
6. A hybridoma producing the monoclonal antibody of claim 1.
7. The hybridoma of claim 6, which is hybridoma 1008-1 or hybridoma 1085-2.
8. A radioimmunoassay of human pancreatic phospholipase A$_2$ using the monoclonal antibody of claim 1.
9. The monoclonal antibody of claim 5, wherein the binding constant of 1008-1 is $4 \times 10^{11}$ M$^{-1}$.
10. The monoclonal antibody of claim 5, wherein the binding constant of 1085-2 is $1 \times 10^{12}$ M$^{-1}$.

* * * * *